United States Patent [19]

Kaufman

[11] 4,389,238

[45] Jun. 21, 1983

[54] FLOWABLE HERBICIDE AND PESTICIDE FORMULATION

[75] Inventor: Harold A. Kaufman, Piscataway, N.J.

[73] Assignee: J. T. Baker Chemical Company, Phillipsburg, N.J.

[21] Appl. No.: 319,558

[22] Filed: Nov. 9, 1981

Related U.S. Application Data

[63] Continuation of Ser. No. 143,368, Apr. 24, 1980, abandoned, which is a continuation-in-part of Ser. No. 925,194, Jul. 18, 1978, abandoned.

[51] Int. Cl.$^3$ ..................... A01N 37/10; A01N 37/38
[52] U.S. Cl. ......................................... 71/115; 71/117; 71/DIG. 1; 424/173; 424/167; 424/361
[58] Field of Search ................... 71/DIG. 1, 117, 115, 71/65, 79

[56] References Cited

U.S. PATENT DOCUMENTS

| 2,893,913 | 7/1959 | Wiedow | 424/213 |
|---|---|---|---|
| 3,322,527 | 5/1967 | Johnson | 71/93 |
| 3,360,356 | 12/1967 | Vartiak | 71/DIG. 1 |
| 3,948,636 | 4/1976 | Marks | 71/79 |
| 4,155,741 | 5/1979 | Scher et al. | 71/DIG. 1 |

FOREIGN PATENT DOCUMENTS

| 736847 | 6/1966 | Canada | 71/DIG. 1 |
|---|---|---|---|
| 7112 | 1/1980 | European Pat. Off. | 71/DIG. 1 |
| 2235959 | 1/1972 | Fed. Rep. of Germany | 71/DIG. 1 |
| 630023 | 10/1949 | United Kingdom | 71/DIG. 1 |

OTHER PUBLICATIONS

Hackh, "Alumina, Aluminum Hydroxide (1972), Hackh's Chem. Dict. pp. 31-32 (1972).
McCutcheon–"Detergents and Emulsifiers" (1970) Allured Pub. Co., pp. 181 and 221 (1970).

*Primary Examiner*—Glennon H. Hollrah
*Attorney, Agent, or Firm*—George W. Rauchfuss, Jr.

[57] ABSTRACT

Novel herbicide and pesticide formulations in flowable form are disclosed and are prepared by combining free acid forms of the active ingredients with unreactive aluminum hydroxide gels.

10 Claims, No Drawings

FLOWABLE HERBICIDE AND PESTICIDE FORMULATION

RELATED APPLICATION

This is a continuation, of application Ser. No. 143,368, filed Apr. 24, 1980, now abandoned which application is a continuation-in-part of earlier application Ser. No. 925,194 filed July 18, 1978 and now abandoned.

FIELD OF THE INVENTION

This invention relates to aluminum hydroxide flowable gel pesticide and herbicide compositions and to the preparation thereof.

BACKGROUND OF THE INVENTION

Commercially available herbicide and pesticide formulations are generally in the form of wettable powders, dusts or granules. However, such formulations are not always desirable as they present problems in handling of the formulations and are particularly irritating to the grower-user. Moreover, many herbicide and pesticide active ingredients are difficult to suspend and thus do not lead to easily produced formulations of the type mentioned. In addition, in the past certain active ingredients that are insoluble organic acids were formed as dialkylamine salts in order to obtain the necessary suspension of the product. However, such dialkylamine salts have the potential of forming highly undesirable nitroso amine derivatives in the environment.

It is, therefore, highly desirable to obtain herbicide and pesticide formulations which avoid one or more of these disadvantages of prior art formulations. Moreover, it would also be advantageous to provide such new and improved herbicide and pesticide formulations which, in addition to avoiding one or more of the prior art problems, also leads to formulations that may possess one or more additional advantages over the prior art formulations.

It has been proposed in the earlier application to obtain such flowable formulations by the use of aluminum hydroxide gel as the suspending agent. However, the use of aluminum hydroxide for the preparation of formulations containing active ingredients such as 2,4-D, dicamba and the like in their free acid form is not entirely suitable and in some cases undesirable because of the chemical reaction that occurs between the acid function of the active ingredient and the aluminum hydroxide. This reaction can cause the initially flowable suspension to set up into a relatively hard mass that is difficult to resuspend and is not an acceptable formulation. In addition, such reaction causes a substantial portion of the active ingredient to be converted to its aluminum salt.

SUMMARY OF THE INVENTION

It has now been discovered that acceptable new and improved flowable herbicide and pesticide formulations of active ingredients in their free acid form may be formed by combining active ingredients in the form of organic acid and of suitable particle size with unreactive aluminum hydroxide gels. It has been found that such unreactive aluminum hydroxide gel herbicide and pesticide formulations in addition to eliminating one or more of the disadvantages of prior formulations also provides formulations that may possess one or more of the following advantages. Formulations of this invention when compared to prior formulations have been shown to possess and retain superior suspending properties, improved crop tolerance, improved control of selected weed species, better handling characteristics than dry dusty wettable powders, an environmental safety advantage over emulsifiable concentrates containing volatile organic carriers and enhanced desiccation defoliation action thereby reducing the amount of pesticide required as a harvest aid.

DETAILED DESCRIPTION OF THE INVENTION

A broad range of novel herbicide and pesticide formulations in flowable form are provided according to this invention by mixing the active ingredients in their organic acid form and of suitable particle size with unreactive aluminum hydroxide gels.

The formulations of the invention are generally prepared by incorporating the appropriate quantity of the active ingredient along with any desired freeze thaw agent, water, and suitable wetting, dispersing and antifoam agents into any suitable mill, or homogenizer such as, for example, an attritor or ball mill, where the ingredients are intimately and homogeneously mixed and the particle size of the herbicide or pesticide is reduced to the desirable particle size range, generally from about 2 to about 5 microns average particle diameter. The mixture, of desired particle size, is then removed from the mill and unreactive aluminum hydroxide gel combined therewith with mixing to yield a generally fluid, homogeneous, very slow settling suspension. Alternatively, the unreactive aluminum hydroxide gel can, if desired, be added directly to the mill for a brief period after the correct toxicant particle size is reached.

Generally unreactive aluminum hydroxide gel, containing approximately about 2 to about 20%, preferably about 6 to about 15% by weight aluminum hydroxide, is employed as the suspending agent at a concentration range of about 5 to about 30%, preferably about 15 to about 25% by weight. The unreactive aluminum hydroxide gel can be used as the sole suspending agent or in combination with other suspending agents, such as for example, methylcellulose, hydroxypropylmethylcellulose, magnesium hydroxide gel, bentonite, Veegum, attapulgite clays, hydroxypropyl guar and the like. The unreactive aluminum hydroxide concentration in compositions of this invention are generally in the range of about 0.10 to about 6.0% by weight aluminum hydroxide (that is, about 0.065 to about 3.9% by weight $Al_2O_3$).

The unreactive aluminum hydroxide gel of this invention which enables active ingredients in their free acid form to be formulated into flowable suspensions is generally prepared by heating a reactive gel suspension of about 4% $Al_2O_3$ concentration at an elevated temperature with good mixing for sufficient time to effect the conversion to unreactive gel.

A suitable starting material for this preparation is a reactive aluminum hydroxide gel such as defined by the U.S.P. XIX. The acid-consuming capacity (ACC) is one measure of the reactivity of aluminum hydroxide gels. The U.S.P. XIX ACC specification is 12.5 to 25.0 ml of 0.1 N hydrochloric acid for one gram of 4% $Al_2O_3$ gel. The theoretical ACC for a completely reactive gel is 23.5 ml and most so-called "reactive" gel typically, show 23.0 to 25.0 ml ACC values. Any excess ACC above the theoretical 23.5 ml value is generally attributed to residual amounts of basic aluminum carbonate and bicarbonate and possible sodium bicarbonate. By comparison, the ACC of the unreactive aluminum hydroxide gel of this invention is only about 1.5 ml, indicating that it is about 94% unreactive by the USP test.

The preferred reactive aluminum hydroxide gel concentration is about 4% $Al_2O_3$ content. Although higher concentrations up to possibly 6% $Al_2O_3$ could be used, the suspension becomes very viscous during the conversion process and maintaining a fluid, agitated suspension at this concentration can be difficult. Concentrations below 4% $Al_2O_3$ can be utilized; however, since the unreactive gel is typically used at a 4% or higher assay, an extra concentration step would be required.

Typical reactive gels are neutral to slightly basic with pH values in the range of 6.5–8.0; these are also suitable pH values for the conversion to unreactive product. It has also been found that the process can be carried out at least up to pH 9.5.

The typical time/temperature conditions used to effect the preparation of unreactive gel is about six hours at 80° C. However, it has also been found that conversion can be completed in only four hours at 80° C. on a laboratory scale.

The unreactive gel can be used as is at the 4% $Al_2O_3$ concentration for incorporation into active ingredient formulations or dewatered to yield a thick paste-like product with about 10% $Al_2O_3$ content. The use of this suspending agent in the preparation of flowable formulations is given in the Illustrative Examples section of this disclosure.

The unreactive aluminum hydroxide gel of this invention differs from typical reactive gels in a number of ways besides the obvious feature of its ability to function as a suspending agent for active ingredients in their free acid form. During the transformation from reactive to unreactive aluminum hydroxide, the gel changes from white to an offwhite appearance. It also undergoes a viscosity increase at this time. This viscosity change is visibly apparent in that a 6% $Al_2O_3$ concentration of reactive gel is a fluid suspension, whereas this concentration of unreactive gel results in a thick nearly non-pourable gel. Also, the relative viscosity values of 4% $Al_2O_3$ suspensions were 1200 cps and 4200 cps for reactive and unreactive gels, respectively.

A key property of the unreactive gel of this invention is its unexpectedly good suspending properties. Aged aluminum hydroxide gels that are unreactive toward 0.1 N hydrochloric acid generally exhibit poorer suspension characteristics than reactive gels. Aging of aluminum hydroxide gels, such as by heating under high alkaline conditions (greater than pH 9) or simply by allowing the gel to age at room temperature for a prolonged time, generally results in its transformation from an amorphous to a crystalline non-reactive material. Preparation of crystalline aluminum hydroxide can also be prepared by direct precipitation at high pH and temperature. Such products usually do not possess suitable suspension properties. The particular conditions under which unreactive gel is prepared as described herein apparently allows the gel to be rendered unreactive toward 0.1 N hydrochloric acid and also active ingredients in their free acid form but still retain good suspending properties. This may be due to a complex polymerization process that stops short of converting the gel to a crystalline state.

Any suitable freeze thaw agent can be employed in the flowable compositions of this invention and is generally present in an amount of from about 1 to about 10% by weight. Among such suitable freeze thaw agents there can be mentioned, for example, urea, polyhydric alcohols such as glycerol, sorbitol, mannitol, ethylene glycol, propylene glycol, polyethylene glycol, glucose, sucrose and the like as well as water soluble nontoxic polymeric agents such as dextran, polyvinylpyrrolidone and the like. Preferred for use in the compositions of this invention is propylene glycol.

Any suitable wetting and dispersing agents may be used in the flowable compositions of this invention and are generally employed in an amount of from about 0.1 to about 6% by weight. Exemplary of suitable wetting and dispersing agents there can be mentioned, for example, non-ionic aromatic polyethylene glycol ethers, such as Antarox A-400, alkyl aryl polyether alcohol type emulsifiers such as Triton X-100, sulfonated purified lignins such as Reax 45A and Reax 45L and a fine mesh, high viscosity, hyproxypropyl guar such as Jaguar HP-8 and the like.

Suitable antifoam agents when employed are used in an amount of from about 0.1 to about 0.5% by weight. Any suitable antifoam agent can be employed such as, for example, a 50% by weight solution of 2,4,7,9-tetramethyl-5-decyn-4,7-diol known as Surfynol 104-E.

As examples of herbicides and pesticides in their organic acid form that may be employed in formulations of this invention there may be mentioned, for example, 3,6-dichloro-2-methoxybenzoic acid, 2,3,6-trichlorobenzoic acid, 2,3,5,6-tetrachlorobenzoic acid, triiodobenzoic acid, 3-nitro-2,5-dichlorobenzoic acid, 2,4-dichloro-3-nitrobenzoic acid, 3-amino-2,5-dichlorobenzoic acid, naphthalene acetic acid, indolebutyric acid, 3,6-endoxohexahydrophthalic acid, α-naphthylphthalamic acid, trichloroacetic acid, 2,2-dichloropropionic acid, 2,3-dichloropropionic acid, 2,2,3-trichloropropionic acid, 4-chlorophenoxyacetic acid, 2,4-dichlorophenoxyacetic acid, 2,4,5-trichlorophenoxyacetic acid, 2-methoxy-3,6-dichlorophenylacetic acid, 3-methoxy-2,6-dichlorophenylacetic acid, 2-methoxy-3,5,6-trichlorophenylacetic acid, β-naphthoxyacetic acid, 3-chlorophenoxypropionic acid, 2,4-dichlorophenoxypropionic acid, 2-methyl-4-chlorophenoxypropionic acid, 2,4,5-trichlorophenoxypropionic acid, 2,4-dichlorophenoxybutyric acid, 2-methyl-4-chlorophenoxybutyric acid, 2,4,5-trichlorophenoxybutyric acid, 4-chloro-2-oxobenzothiozolin-3-yl acetic acid, and 4-amino-3,5,6-trichloropicolinic acid and the like. It will be appreciated that the foregoing examples are merely exemplary of the many free acid form herbicidal and pesticidal active ingredients that may be formulated in the compositions of this invention. In the formulations of this invention the active ingredient will generally be present in an amount of from about ½ to about 8 pounds and preferably about 3 to 5 pounds of active ingredient per gallon of formulation.

The compositions can also comprise such additional substances as other herbicides, pesticides, such as insecticides, nematocides, fungicides, and the like; stabilizers, spreaders, deactivators, adhesives, stickers, fertilizers, activators, synergists, and the like. That is, the compositions of the present invention are also useful when other herbicides, pesticides and/or defoliants, dessicants, growth regulants, and the like are also included in the herbicidal and pesticidal compositions heretofore described. These other materials can comprise from about 5% to about 95% of the active ingredients in the herbicidal compositions. Use of combinations of these other herbicides, pesticides, and/or defoliants, dessicants, etc. with the compounds of the present invention provide herbicidal compositions which are more effective in controlling weeds and often provide results unattainable with separate compositions of the individual herbicides and pesticides. The other herbicides, defoliants, desiccants and plant growth regulants which can be used as compositions of this invention can include chlorophenoxy herbicides such as 4(2,4-DB), 2,4-DEB, 4-CPB, 4-CPA, 4-CPP, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atratone, desmetryne, norazine, ipazine, prometryn, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as sodium 5-[2-chloro-4-(trifluoromethyl)-phenoxy]-2-nitrobenzoate and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2(3,4-dichloro-phenyl)-4-methyl-1,2,4-oxabdiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamide, DEF, ethyl xanthogen disulfide, sindone, sindone B, propanil and the like.

Such herbicides and pesticides can also be used in the compositions of this invention in the form of their salts, esters, amides and other derivatives whenever applicable to the particular parent compounds.

The flowable system of this invention provides a unique liquid carrier and suspension system which obviates the need for the preparation of dialkylamine salts which have the potential of forming undesirable nitroso amine derivatives. Moreover, when formulated as a flowable composition of this invention the active ingredient will generally exhibit improved herbicidal or pesticidal performance over use of the free acid according to prior art compositions.

As examples of formulations according to this invention reference may be had to the following illustrative examples.

EXAMPLE 1

Aluminum hydroxide gel, a reactive gel conforming to USP XIX specifications, was diluted to 4% $Al_2O_3$ content with deionized water. The suspension was agitated and brought to 80° C. and maintained at that temperature for about six hours. The total volume was maintained approximately constant by periodic water additions, as necessary, to replace water lost by evaporation. After six hours, the suspension was cooled to room temperature and incorporated into a flowable pesticide formulation as follows.

Into an Attritor model 01 mill containing about 4 lbs. of ⅛ inch stainless-steel balls were added 100 g water and 8.9 g propylene glycol. The mill was activated and 6.7 g Reax 45A and 191 g 2,4-D were alternately added over about a 5 minute period. Milling continued until the 2,4-D particle size was reduced to 3–5 microns average particle diameter. The mixture was removed from the mill and the appropriate amount of unreactive aluminum hydroxide gel, Jaguar HP-8 initially hydrated with water and water were added and blended thoroughly to give a stable, flowable suspension with the following composition:

| Component | Weight % |
|---|---|
| 2,4-D | 43.0 |
| Reax 45-A | 1.5 |
| Propylene Glycol | 2.0 |
| Aluminum Hydroxide Gel (10% $Al_2O_3$ assay) | 9.0 |
| Jaguar HP-8 | 0.2 |
| Antifoam agent | 0.1 |
| Water | 44.2 |
| | 100.0 |

EXAMPLE 2

Two hundred grams of a reactive aluminum hydroxide gel containing 10% $Al_2O_3$ was diluted with 300 grams of deionized water and thoroughly mixed to prepare a 4% $Al_2O_3$ suspension. With continuous agitation, the suspension was brought to 80° C. and maintained at that temperature for six hours. Periodic additions of water were made in order to replace the water lost through evaporation. The inactivated gel was then removed from the heat source, cooled to room temperature, and filtered to remove the free water and yield a viscous gel containing about 10% $Al_2O_3$.

A formulation containing the inactive aluminum hydroxide gel as a suspending agent for dicamba was prepared in the following manner. Appropriate amounts of dicamba, water, propylene glycol and Reax 45A wetting-dispersing agent were added to an Attritor model 01 mill containing ⅛ inch stainless-steel balls and milled until the dicamba particle size was reduced to 3–5 microns average particle diameter. The mixture was removed from the mill and unreactive aluminum hydroxide gel, Jaguar HP-8 and water were added and the mixture thoroughly blended to give a flowable suspension having the following composition:

| Component | Weight % |
|---|---|
| Dicamba | 37.5 |
| Reax 45A | 1.0 |
| Propylene Glycol | 1.8 |
| Aluminum Hydroxide Gel (10% $Al_2O_3$ assay) | 9.0 |
| Jaguar HP-8 | 0.1 |
| Surfynol 104E | 0.1 |
| Water | 50.5 |
| | 100.0 |

The improved suspending properties of the unreactive gel of this invention over reactive gel from which it is prepared can be seen from the following comparison. Suspensions of reactive and unreactive gels at 1.8% $Al_2O_3$ concentration were prepared by diluting the approximately 10% $Al_2O_3$ starting gels with deionized water and thoroughly mixing to obtain a homogenous suspension. The suspensions were allowed to stand at room temperature and the amount of aluminum hydroxide remaining in suspension was measured periodically.

The following results were obtained:

|  | % Gel suspended | | |
| --- | --- | --- | --- |
|  | 1 Week | 2 Weeks | 7 Weeks |
| Reactive Gel | 74 | 71 | 69 |
| Unreactive Gel | 95 | 95 | 95 |

It can be seen that about 38% more unreactive gel remains in suspension than reactive gel after standing for seven weeks.

I claim:

1. A flowable toxicant composition comprising (a) an effective amount of a water-insoluble active pesticide in its free acid form having a herbicide size of from about 2 to about 5 microns average particle diameter and (b) from about 5 to about 30% by weight unreactive aluminum hydroxide gel containing about 2 to 20% by weight aluminum hydroxide which has been rendered unreactive by heating at an elevated temperature with mixing for sufficient time to effect its conversion to unreactive gel without loss of its suspending properties.

2. The composition of claim 1 wherein there is present from about 1 to about 10% by weight of a freeze thaw agent and from about 0.1 to about 6% by weight of a wetting and dispersing agent.

3. The composition of claim 2 wherein there is present from about 0.1 to about 0.5% by weight of an antifoam agent.

4. The composition of claim 3 wherein the freeze thaw agent is selected from the group consisting of urea, glycerol, sorbitol, mannitol, ethylene glycol, propylene glycol, polyethylene glycol, glucose, sucrose, dextran and polyvinylpyrrolidone.

5. The composition of claim 4 wherein the wetting and dispersing agent is selected from the group consisting of non-ionic aromatic polyethylene glycol ethers, alkylaryl polyether alcohols and sulfonated purified lignins.

6. The composition of claim 3 wherein the antifoam agent is a 50% by weight solution of 2,4,7,9-tetramethyl-5-decyn-4,7-diol.

7. The composition of claim 1 wherein the active ingredient is selected from the group consisting of 2,4-dichlorophenoxyacetic acid and 3,6-dichloro-2-methoxybenzoic acid.

8. The composition of claim 1 wherein the active ingredient is present in an amount of from about ½ to about 8 pounds per gallon of composition.

9. The composition of claim 1 which is

| Component | Weight % |
| --- | --- |
| 2,4-dichlorophenoxyacetic acid | 43% |
| Sulfonated purified lignin | 1.5 |
| Propylene glycol | 2 |
| Aluminum hydroxide gel (10% $Al_2O_3$ assay) | 9.0 |
| Hydroxypropyl guar | 0.2 |
| Antifoam agent | 0.1 |
| Water | 44.2 |
|  | 100.0 |

10. The composition of claim 1 which is

| Component | Weight % |
| --- | --- |
| 3,6-dichloro-2-methoxybenzoic acid | 37.5% |
| Sulfonated purified lignin | 1.0 |
| Propylene glycol | 1.8 |
| Aluminum hydroxide gel (10% $Al_2O_3$ assay) | 9.0 |
| Hydroxypropyl guar | 0.1 |
| Antifoam agent | 0.1 |
| Water | 50.5 |
|  | 100.0 |

* * * * *